United States Patent [19]

Bean, III et al.

[11] Patent Number: 4,952,062

[45] Date of Patent: Aug. 28, 1990

[54] METHOD AND APPARATUS FOR DETECTING FLAWS IN FABRIC

[76] Inventors: Vern W. Bean, III, 132 Hazel Way; Thomas H. Borders, 122 Ashling Dr.; Thomas M. Turner, Jr., 235 Westwood Dr., all of LaGrange, Ga. 30240

[21] Appl. No.: 228,436

[22] Filed: Aug. 5, 1988

[51] Int. Cl.$^5$ .................................... G01N 21/89
[52] U.S. Cl. .................................... 356/430; 250/562; 250/572
[58] Field of Search .................. 356/238, 429, 430; 250/562, 572

[56] References Cited

U.S. PATENT DOCUMENTS

| | | | |
|---|---|---|---|
| 3,001,080 | 9/1961 | Neil | 250/562 |
| 3,835,332 | 9/1974 | Bridges | 356/430 X |
| 3,841,761 | 10/1974 | Selgin | 356/430 |
| 4,249,081 | 2/1981 | Cole et al. | 250/572 X |

*Primary Examiner*—Davis L. Willis
*Assistant Examiner*—Matthew W. Koren
*Attorney, Agent, or Firm*—Thomas & Kerr

[57] ABSTRACT

A method and apparatus for detecting flaws in web material such as fabric comprises an array of optical sensors arranged in closely spaced relationship into at least one row spanning the web to be inspected. A light source is mounted in spaced parallel relationship relative to the sensor array and the web passes between the light source and the sensors. Each sensor produces a voltage signal that is proportional to intensity of light falling thereon and, therefore, to the amount of light transmitted by the portion of the web passing adjacent the sensor. The sensors are connected to a microprocessor that is programmed to compare their signals to standards representing signals produced by flawless fabric. A predetermined number of comparison results are combined and transformed into a single representative value that is compared with a preselected threshold value. If the representative value exceeds the threshold, a signal indicative of a flaw is produced by the microprocessor.

19 Claims, 4 Drawing Sheets

METHOD AND APPARATUS FOR DETECTING FLAWS IN FABRIC

TECHNICAL FIELD

The present invention relates to flaw detection, and more particularly, to a method and apparatus for detecting flaws in tufted, woven or knitted fabric as the fabric leaves the loom.

BACKGROUND OF THE INVENTION

In modern textile mills, fabric or cloth is commonly tufted, woven or knitted in predetermined widths on high-speed, automated looms. It is common in such processes for a thread supplying the loom to break resulting in a flaw commonly known as an "out" in the fabric. Supply threads can also become entangled or misplaced in the fabric resulting in flaws known as "slubs". It is important that such flaws be detected soon after the cloth leaves the loom so that the loom can be stopped and the defect causing the flaw corrected.

In the past, such flaws have been detected through manual visual inspection by the operator of the loom. Such manual inspection has often proven to be inefficient and has become increasingly more difficult as the speed of modern looms has increased. In addition, manual detection of flaws in fabric having patterns or designs knitted therein is often even more difficult.

Automated optical scanning devices for detecting flaws in fabric as it leaves the loom have been developed. In general, these devices comprise means for illuminating one side of the fabric and means for detecting the intensity of light that is transmitted by the fabric. The detecting means has included moving or scanning type sensors such as those illustrated in U.S. Pat. Nos. 4,702,283 of Shaw and U.S. Pat. No. 3,410,643 of Jorgensen. These types of sensors tend to have many mechanical moving parts and are prone to require frequent adjustment and repair. In addition, such scanning detectors only inspect the fabric in zig-zag lines across the width of the fabric such that the entire surface of the fabric is not inspected.

Detectors comprising arrays or lines of optical sensors that inspect the entire width of the fabric as it leaves the loom have also been developed. U.S. Pat. No. 3,001,080 of Neil illustrates a device using such a sensor array.

It has been common, when using both scanning sensors and sensor arrays, to compare the intensity of light falling on each sensor to a predetermined value and, if the difference between the detected intensity and the predetermined value exceeds a preset difference, to produce a signal that stops the loom or activates an alarm so that the loom can be adjusted or repaired. It is common for the predetermined value and preset difference used for comparison to be preset manually by the operator as illustrated in the patent to Neil.

Prior art methods of detecting flaws in material, while representing improvements in the art, have not always proven acceptable. In particular, the prior art methods tend to perform poorly when detecting flaws in material having designs or patterns dyed or knitted into the material. This is because the designs themselves can cause extreme variations in the intensity of light transmitted by the material with such variations causing prior art methods to signal falsely a flaw in the material. This is particularly true for scanning type sensors that only inspect a fraction of the surface of the material.

In addition, even when used with fabric having no design, prior art devices tend to stop the loom upon a single detection of an unusually high or low intensity. This often causes the loom to be stopped for insignificant or acceptable flaws or because of an anomalous sensor reading resulting in costly time delays.

Accordingly, it is to the provision of a method and apparatus for detecting flaws in knitted fabric that overcomes the problems of the prior art that the present invention is primarily directed.

SUMMARY OF THE INVENTION

The present invention is an apparatus and method for detecting flaws in web material and particularly in tufted, woven or knitted fabric. The apparatus comprises an array of optical sensors arranged in closely spaced relationship into at least one row having a length corresponding to the width of the fabric to be inspected. Means for illuminating each sensor in the array is provided and the fabric to be inspected passes between the illuminating means and the sensor array. A portion of the light from the illuminating means is transmitted through the fabric and impinges on the sensors. Each sensor produces a voltage signal that is proportional to the intensity of light falling thereon. The variation in the voltage signal of each sensor as the fabric moves past the array is, therefore, a measure of the changing transmissivity of the portion of the fabric passing adjacent the sensor. A flaw or defect in the fabric, such as a missing thread or "out", typically causes the average transmissivity of the fabric to change at the location of the flaw and a corresponding change in the signal of the sensor adjacent the flaw results.

The sensors are connected to a microprocessor that is programmed to sample repeatedly the voltage signal produced by each sensor as the fabric passes the array. As each sample is made, the signal is compared to a norm or standard for that sensor representing signals ordinarily resulting from fabric having no flaws. A factor characteristic of the degree of deviation of each sample from the standard is added to a running total of such factors and when the running total for a sensor exceeds a predetermined value, the microprocessor produces an alert signal indicating that a flaw has been detected and displays the location of the sensor detecting the flaw. Further, only a predetermined number of past samples contribute to the running total so that the decision to produce an alert signal is not influenced by older factors. While the alert signal is ordinarily used to stop the loom to allow the flaw to be corrected, it can also be used for other purposes if desired such as, for example, to sound an alarm.

The standard of comparison for each sensor is generated by passing fabric that is known to have no flaws between the light source and the sensors and sampling a large number of voltage signals for each sensor. The standard, then, becomes the average value of these samples and the standard deviation of the samples becomes a measure of normally occurring deviations in the flawless fabric. Standards thus created incorporate signal variations resulting from designs or patterns in the fabric into the standard deviation. The microprocessor in effect "learns" the pattern in the fabric such that variations in subsequently sampled signals that result from the design in the fabric itself are not misclassified as flaws. Unlike prior art devices, therefore, the method and apparatus of the present invention detects flaws in fabrics having patterns knitted or dyed therein and, further, is easily adaptable to other patterns by simply creating new standards using fabric containing new patterns. In addition, the apparatus has no moving parts to require maintenance, alignment or repair.

Thus, a method and apparatus for detecting flaws in knitted fabric is provided that has no moving parts and that, unlike the prior art devices and methods, accurately detects flaws in fabric having patterns or designs therein. The unique method of processing the signals produced by the sensors ensures that the loom is stopped only when a detected flaw is sufficiently severe and spatially extensive to merit correction. Time consuming and expensive delays for insignificant or acceptable flaws or anomalous readings are therefore dramatically reduced. Other objects, features and advantages of the invention will become apparent upon reading the specification in conjunction with the accompanying drawings.

DETAILED DESCRIPTION

Figure 1:
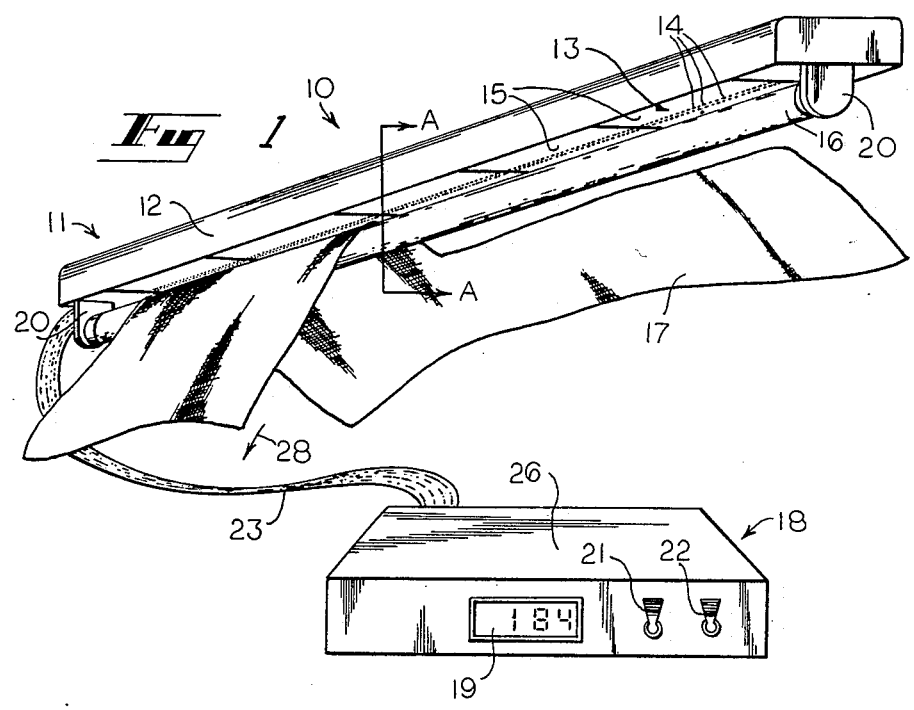
FIG. 1 is a perspective view of apparatus embodying principles of the invention in a preferred form in which a length of fabric is shown passing between the fluorescent bulb and the sensor array of the apparatus.

Referring now in more detail to the drawings in which like numerals represent like parts throughout the several views, FIG. 1 shows an apparatus 10 for detecting flaws in knitted fabric. The apparatus comprises a fabric inspection unit 11 and an information processor and control unit 18. The fabric inspection unit 11 has a sensor array housing 12 made of a suitable material such as, for example, aluminium. The housing 12 is formed in the shape of an inverted channel having an open lower side. Securely mounted in the open lower side of the channel are a plurality of sensor support boards 15 that carry a sensor array 13 and sensor interface electronics 24 (FIG. 2), as described in more detail below.

Mounted to the end portions of the housing 12 and extending below the lower side thereof are fluorescent bulb support sockets 20 for receiving and supporting a fluorescent light bulb 16 for illuminating the sensors in the array. The support sockets 20 and bulb 16 are of a conventional construction and are powered by a conventional ballast (not shown) to produce light. It is desirable that the ballast be of the high frequency type such that variations in sensor output due to changing bulb intensity are minimized. It has been found that a ballast operating at 25,000 cycles per second performs satisfactorily for detecting flaws in knitted fabric.

As shown in FIG. 1, a fabric 17 to be inspected extends between the bulb 16 and the sensor array 13. Normally, the fabric passes through the sensor assembly as it leaves the loom. In this way, defects are detected soon after they occur so that the loom can be stopped and the defect corrected.

Information processor and control unit 18 comprises a housing 26 containing a microprocessor and power supply. Display element 19, start switch 21 and calibrate switch 22 are provided to allow an operator to interface with the unit. A numeric key pad (not shown) can be provided if desired to allow the operator to enter numeric information into the microprocessor.

Figure 2:
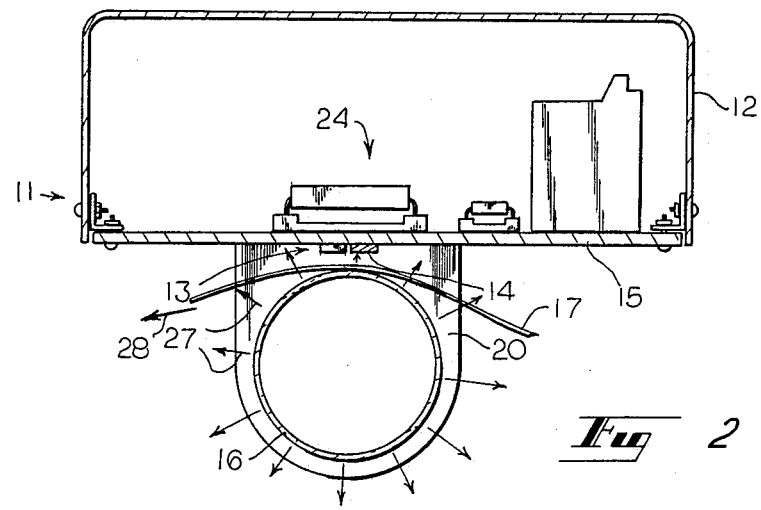
FIG. 2 is a cross-sectional view taken along line AA in FIG. 1.

FIG. 2 is a cross-sectional view taken along line AA of FIG. 1. Housing 12 is seen to support sensor support board 15 and to contain multiplexing electronics 24. A sensor array 13, comprising two rows of a plurality of individual sensors 14, is attached to the bottom of the sensor support board 15, as shown. The fluorescent bulb 16 extends parallel to the sensor array and is spaced therefrom such that a width of fabric 17 can move longitudinally in the direction indicated at 28 between the bulb and the sensor array as it leaves the loom.

Some of the light, generally indicated at 27, that is emitted by that light bulb, impinges upon the fabric 17 and a portion of the light is transmitted by the fabric to fall on the sensors 14 of the sensor array 13. The light that is transmitted by the cloth is a function of the transmissivity of the fabric. It can be seen, therefore, that the intensity of the light falling on a particular sensor 14 indicates the transmissivity of the portion of the fabric passing adjacent that sensor. Typically, a flaw or defect in the fabric such as a missing thread or "out" will cause the average transmissivity of the fabric to change at the location of the flaw and a corresponding change in the signal of the sensor adjacent the flaw will result.

Figure 3:
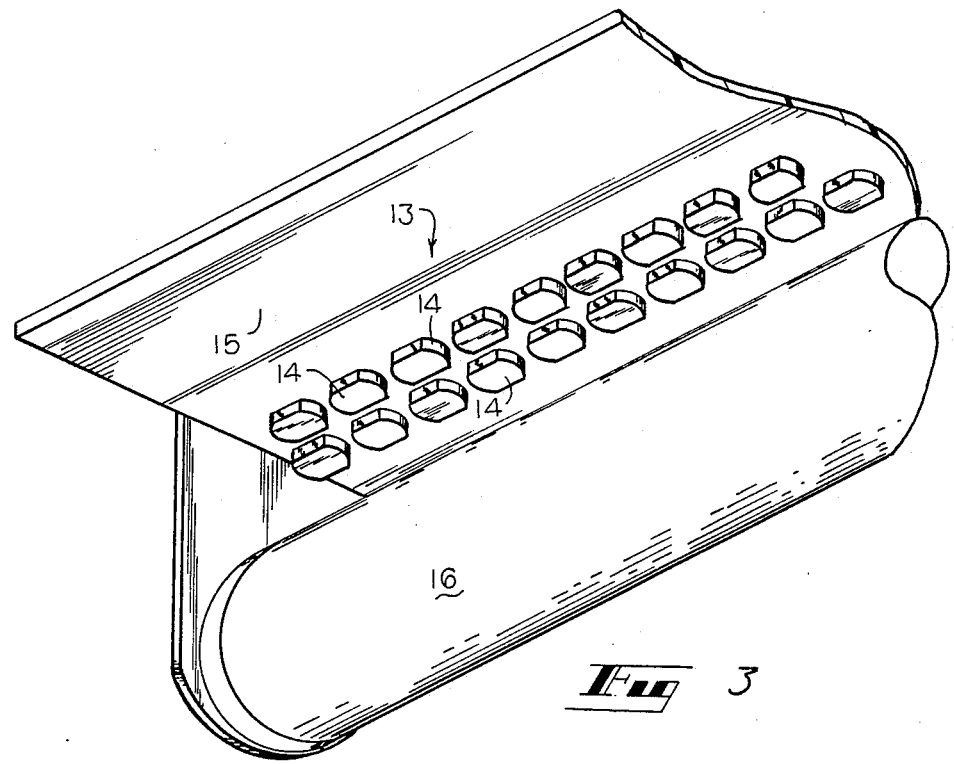
FIG. 3 is a perspective view, partially in section, showing the arrangement of sensors in the sensor array.

FIG. 3 is a detailed view of the underside of the sensor support board 15 showing the configuration of the sensors 14. The sensors 14 are arranged in closely spaced relationship into two rows with each sensor in the second row being staggered or offset from adjacent sensors in the first row. With this configuration, portions of the fabric passing between two sensors in the first row, thereby escaping inspection by the first row of sensors, will pass adjacent a sensor in the second row and be inspected by that sensor. The entire area of the fabric, therefore, is inspected as it passes adjacent the sensor array 13.

While various types of optical sensors may be suitable, it has been found that a photoresistor of type CL9T9LL, manufactured by Clairex Electronics performs well. In addition, it has been found that a sensor density of approximately 10 sensors per inch provides sufficient resolution to detect flaws of the type characteristically occurring in fabric.

Figure 4:
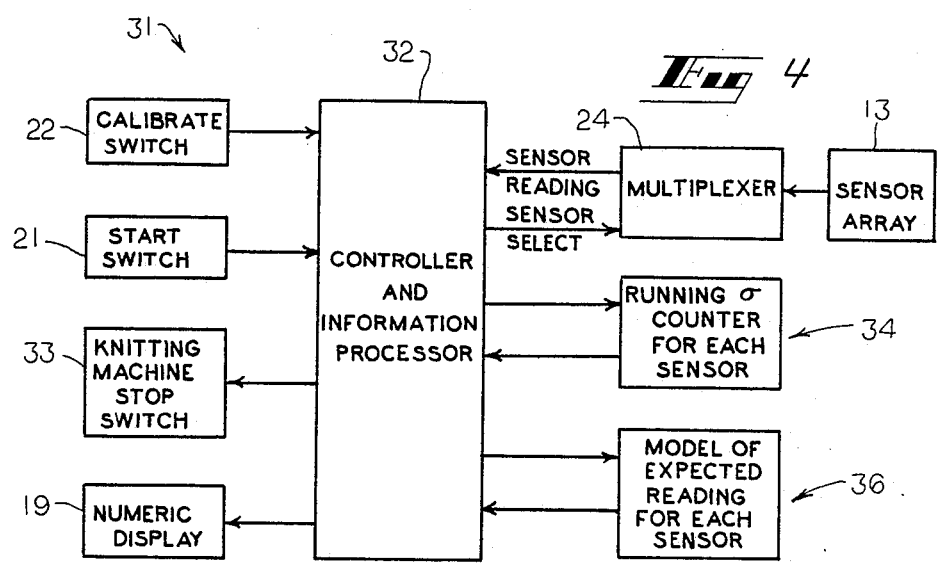
FIG. 4 is a blocked diagram of the invention illustrating the major parts thereof.

FIG. 4 is a block diagram of the preferred embodiment illustrating the major components and functions. A central component here is the controller and information processor 32 that comprises a microprocessor and its related circuitry. While many available microprocessors could perform the required tasks, it has been found that a microprocessor of the 80188 family, manufactured by the Intel Corporation, is particularly well suited because of its speed and ability to accept signals from 16 sensors simultaneously. The start switch 21 and the calibrate switch 22 are adapted to produce a signal when depressed by an operator which is readable by the microprocessor. The start switch is depressed to initiate inspection of fabric and the calibrate switch is depressed to initiate the building of standards representing flawless fabric, as discussed below.

The controller 32 can display useful information on numeric display 19 such as, for example, the number of a sensor detecting a flaw. In addition, the controller 32 is adapted to interface with the loom or knitting machine stop switch 33 such that the loom can be stopped upon the detection of a flaw in the fabric.

Figure 6:
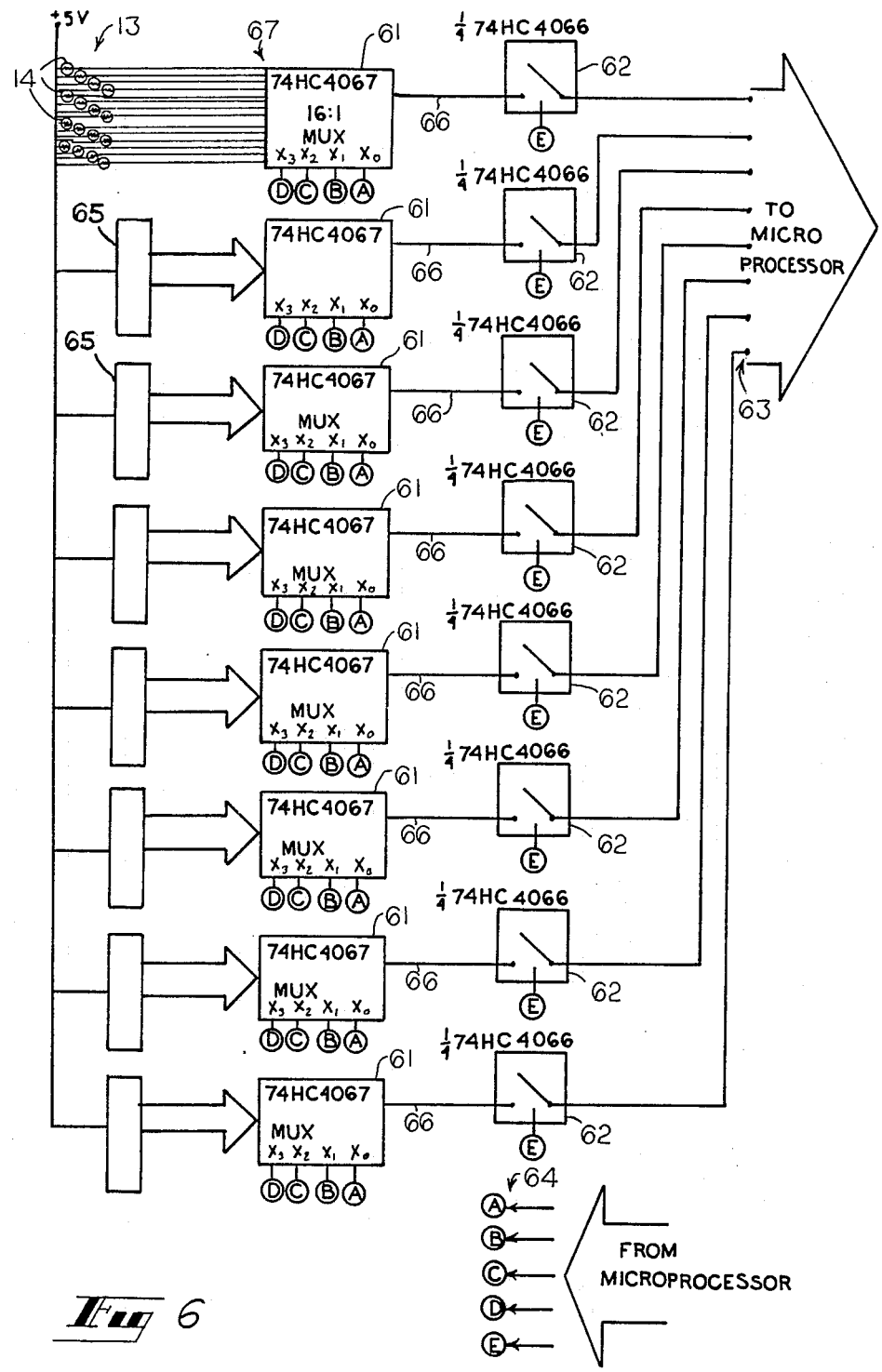
FIG. 6 is a schematic diagram of the sensor array interface electronics.

The sensor array 13 is interfaced to the microprocessor 32 through a multiplexer circuit 24 (FIG. 6). The multiplexer circuit allows the microprocessor to select a group of 16 sensors in the array whose signals are directed to the microprocessor for analysis.

A model of expected readings or standard for each sensor 36, and a running deviation total counter for each sensor 34, are maintained by the microprocessor controller, as described below.

FIG. 6 is an electronic schematic illustrating a preferred method of interfacing the sensor array 13 to the microprocessor. While only one sensor support board 15 is illustrated in FIG. 6, it will be understood that several such boards typically are used in a complete sensor array, as shown in FIG. 1. Each sensor support board 15 supports 128 optical sensors electrically arranged into eight groups of 16 sensors as indicated at 65. Each board 15 comprises eight multiplexer chips 61 and eight latch switches 62. Each multiplexer chip has 16 input lines generally indicated at 67, an output line 66 and four address lines A, B, C and D. In general, the combination of high and low voltage levels appearing at address lines A, B, C and D represents one of 16 binary numbers in the range zero to fifteen and selects one of the 16 input lines as shown in Table 1 below. Here the numeral 1 indicates a high voltage level (e.g. 5 volts), and the numeral 0 indicates a low voltage level (e.g. 0 volts).

TABLE 1

| Input Selection | | | | |
| --- | --- | --- | --- | --- |
| A | B | C | D | SELECTS |
| 0 | 0 | 0 | 0 | 0 |
| 0 | 0 | 0 | 1 | 1 |
| 0 | 0 | 1 | 0 | 2 |
| 0 | 0 | 1 | 1 | 3 |
| 0 | 1 | 0 | 0 | 4 |
| 0 | 1 | 0 | 1 | 5 |
| 0 | 1 | 1 | 0 | 6 |
| 0 | 1 | 1 | 1 | 7 |
| 1 | 0 | 0 | 0 | 8 |
| 1 | 0 | 0 | 1 | 9 |
| 1 | 0 | 1 | 0 | 10 |
| 1 | 0 | 1 | 1 | 11 |
| 1 | 1 | 0 | 0 | 12 |
| 1 | 1 | 0 | 1 | 13 |
| 1 | 1 | 1 | 0 | 14 |
| 1 | 1 | 1 | 1 | 15 |

The signal of the optical sensor connected to the input line corresponding to the binary number represented at the address lines is caused by the multiplexer to appear on the output line 66. This signal is transmitted along data lines 63 when latch 62 is activated by an application of a voltage signal to its enable line E. In the preferred embodiment, the sensors are photoresistors whose electrical resistance varies as a function of the intensity of light falling thereon. Each photoresistor is connected in series between an input line of the multiplexer and a five volt power source such that the signal appearing at the input line varies within the range zero to five volts and is proportional to the intensity of light falling on the photoresistor. The microprocessor is connected to data lines A, B, C and D and to enable line E such that the microprocessor may specify or select a sensor and enable the latches.

In operation, the microprocessor first sets the address lines to correspond to, for example, the first sensor of each group of 16 sensors causing the voltage signal from the first sensor of each group to appear at output lines 66. The microprocessor then activates the enable line E of each of the latches by causing a high voltage (e.g. 5 volts) to appear on those lines. This causes the voltage signals of the first sensor of each group to be transmitted along lines 63 to the microprocessor where they are analyzed, as previously discussed. Succeeding sensors are then selected by the microprocessor in the same way until the signal of each sensor has been analyzed.

Since the microprocessor can accept 16 inputs simultaneously, two sensor support boards are typically activated at the same time. The principle, however, is the same as just discussed for a single sensor board.

Further, while many multiplexer chips and latches are available, it has been found that multiplexers of the type CD74HC4067E manufactured by RCA, coupled with latches of the type CD74HC4066E by RCA, perform well in the circuit of FIG. 6.

OPERATION

Figure 5:
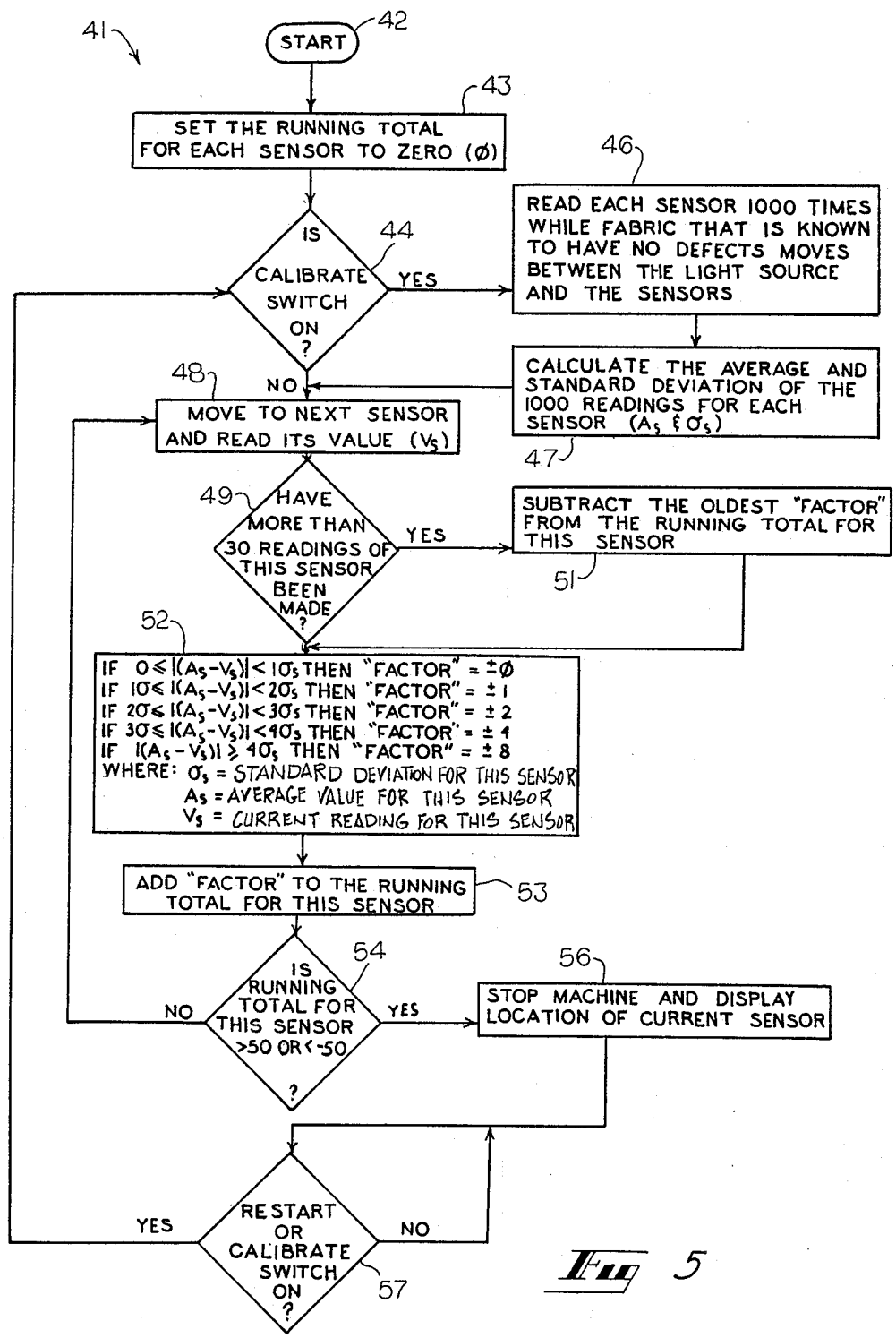
FIG. 5 is a functional flow chart showing the method of processing signals produced by the sensor array.

The unique method of processing the information available from the sensors is shown in the functional flowchart of FIG. 5. The first function usually performed by the system is that of establishing standards that represent sensor readings corresponding to unflawed fabric. This process is represented by functional blocks 46 and 47 in FIG. 5. Typically, an operator will cause a length of fabric that is known to have no flaws to move between the light source 16 and the sensor array 13 and depresses the calibrate switch. As this unflawed fabric moves beneath the sensors at the rate that it normally leaves the loom, each sensor signal is sampled a large number of times (e.g., 1000 times). An average value for all of the readings for each sensor is calculated along with a standard deviation of the readings and this information is stored in the microprocessor. The average and standard deviation for each sensor represents the standard or expected average and range of readings for that sensor for fabric containing no flaws.

After standards for each sensor using known flawless fabric have been generated and stored, the process of inspecting fabric of unknown quality can be initiated through depression of the start switch. This process begins with functional block 48 in FIG. 5 in which the microprocessor activates the sensor support boards, as discussed above, causing the multiplexer circuitry to return the signal from the next set of 16 sensors in the sensor array for an analysis of the signal from each of the sensors. Next, if more than a predetermined number of readings (e.g., 30) of the sensor currently being analyzed have been made, the contribution of the oldest reading is removed from the decision-making process by subtracting its associated "factor" from the running total, as indicated in functional blocks 49 and 51. This "moving time window" of sensor readings is important and will be discussed in more detail below.

The next step of the process is to compare the sensor signal of the current sensor to the stored standard for the current sensor as indicated in functional block 52. As can be seen in this functional block, if the magnitude of the difference between the current sensor signal and the average expected signal for this sensor is between zero and one standard deviation, then a variable called "factor" is set to zero. If the magnitude of the difference is between one standard deviation and two standard deviations, then "factor" is set to +1 if the sensor signal is greater than the average or −1 if the signal is less than the average. If the magnitude of the difference is between two and three standard deviations, "factor" is set to +2 or −2 and if between three and four standard deviations, "factor" is set to +4 or −4. For all measurements falling more than four standard deviations away from the average expected value, factor is set to +8 or −8, depending upon whether the signal is greater than or less than the average.

In functional block 53, the value of "factor" resulting from the comparison of the current sensor signal with the standard for that sensor is added to the running total for the sensor. As indicated in functional block 54, if the running total for the current sensor exceeds a predetermined number, for example, 50, then the loom is stopped and the number of the current sensor is displayed on the numeric display 19. If the running total for the current sensor has not exceeded the predetermined value, then the comparison process begins for the next sensor.

The signal from each sensor in the array is sampled and analyzed as discussed in relatively rapid succession (e.g., 5 times per second). As fabric having no flaws passes between the light source and the sensor array, the accumulated signals from each sensor will tend to average to the expected average represented by the standard for that sensor. This means that the number of signals greater than the average will be substantially the same as the number that are less than the average and further that the magnitudes of their differences from the average will be substantially the same. It can be seen, then, that if no flaw occurs in the fabric adjacent a sensor, the running total for that sensor, while it will fluctuate from signal to signal, will tend to average to zero. It will not tend to approach the threshold value (e.g., 50 or −50) and will not, therefore, cause the microprocessor to signal a flaw.

If, however, a continuous flaw such as an "out" appears in the fabric adjacent a sensor, the transmissivity of the fabric will increase along the location of the flaw because of the missing thread. Consequently, the intensity of light falling on the sensor will increase. This means that the number of signals that are greater than the expected average will increase relative to the number that are less than the average. The ratio of the magnitudes of their respective differences will, at the same time, become greater than one. As a consequence, it can be seen that relatively more and larger positive "factors" will be added to the running total causing the running total eventually to exceed the threshold (e.g., 50) causing the microprocessor to signal a flaw and stop the loom. The same result is caused by a flaw such as a "slub" which decreases the intensity of the light falling on the sensor causing an increase in the number of negative "factors" that are added to the running total, eventually causing the total to exceed minus fifty, again stopping the loom.

If a running total for a sensor exceeds the threshold value indicating a flaw, the microprocessor simply waits, as indicated at functional block 57, until either the restart or calibrate switch is activated by the operator. Upon activation of either of these switches, control is transferred to functional block 44 where the fabric inspection process begins again.

The unique implementation of the moving "time window" illustrated in functional blocks 49 and 51, in combination with the running total representing deviations from expected average readings, ensures that the loom is only stopped if a detected flaw is unacceptably severe or spacially extensive, and that erroneous or single large or small signals do not affect the running total after a predetermined number of subsequent normal signals. With the embodiment illustrated in FIG. 5, it can be seen that even a severe sensor signal having a magnitude of more than four standard deviations from the average expected value will not cause the loom to be stopped but will only add or subtract a factor of eight to the running total. Only if subsequent signals also indicate a flaw will the running total tend to approach and exceed the threshold (e.g., 50) causing the machine to be stopped.

It can be seen, then, that in order for the loom to be stopped, a flaw or defect in the fabric must either be extremely severe for a short period of time or more subtle for a longer period of time. In addition, the moving "time window" of functional block 51 wherein factors resulting in measurements more than 30 samples old are subtracted from the running total, ensures that erroneous or extreme but non-continuous signals do not influence the decision-making process after 30 subsequent normal signals.

In the preferred embodiment illustrated in FIG. 5, the "time window" consists of 30 readings of a sensor, the running total thresholds are illustrated to be 50 and −50 and the factors added to the total resulting from the measurements are as illustrated in functional block 52. It will be understood by persons of skill in the art that these numbers are only examples and can be changed to provide other desirable results. For example, the running total threshold could be increased to 100 with the result that a detected flaw would have to be twice as severe or last twice as long to result in machine stoppage. Similar results can be achieved by reducing the "factors" corresponding to each measurement deviation in functional block 52.

The invention has been described in terms of a preferred embodiment used to detect flaws in fabric.

It will be understood by those of skill in the art that the method and apparatus embodying the invention can take various forms and can be used to detect flaws in various other materials as well. For example, the invention may be used to detect flaws in other web materials such as paper or in materials such as glass. In addition, the invention works equally well with light reflected from the surface of a material rather than transmitted through the material making the invention useful for detecting flaws in, for example, sheet metal or other opaque materials. Other additions, deletions and modifications may be made without departing from its spirit and scope of the invention as set forth in the claims.

What is claimed is:

1. In the method of examining a web of fibrous material for the presence of flaws wherein measurements indicative of the intensity of light transmitted through the web are compared with a range of measurement values indicative of the intensity of light transmitted by a web of acceptable quality, THE IMPROVEMENT COMPRISING the steps of determining the difference between each measurement and a preselected value within the range, adding each determined difference to a running total of such differences and producing a signal when the running total exceeds a preselected limit indicative of the presence of a flaw.

2. The improvement of claim 1 further comprising the step of subtracting a determined difference from the running total when a preselected number of subsequent differences have been added to the total.

3. A method of detecting flaws in fabric comprising the steps of:
   establishing a standard indicative of the intensity of light transmitted by fabric of acceptable quality;
   illuminating the fabric;
   making a plurality of successive measurements of the intensity of light transmitted by the fabric;
   comparing each successive measurement with the standard and establishing a factor characteristic of the difference between the measurement and the standard;
   adding each factor to a running total of such factors;
   comparing the running total with a preselected limit indicative of a flaw; and
   producing a signal when the running total exceeds the preselected limit.

4. The method of claim 3 wherein the step of comparing the running total with a preselected limit is performed as each factor is added to the running total.

5. The method of claim 3 further including the step of subtracting the factor characteristic of a difference from the running total when a preselected number of subsequent factors characteristic of subsequent differences have been added to the running total.

6. The method of claim 3 wherein the step of establishing a standard comprises the steps of:
   illuminating a sample of the fabric known to be of acceptable quality;
   making a plurality of measurements of the intensity of light transmitted by the sample;
   calculating the average value of the plurality of measurements; and
   calculating the standard deviation of the plurality of measurements.

7. The method of claim 6 wherein the step of comparing each successive measurement with the standard comprises the step of determining the difference between the measurement and the average value, and expressing the difference in units of the calculated standard deviation.

8. The method of claim 3 further including the step of moving the fabric along a path and wherein the plurality of successive measurements of the intensity of light transmitted by the fabric are made along at least one line substantially parallel to the direction of movement of the fabric and wherein the distance between each successive measurement substantially corresponds to the mesh size of the woven fabric.

9. A method of detecting flaws in fabric, said comprising the steps of:
   establishing a standard indicative of an optical property of fabric of acceptable quality;
   moving fabric to be examined past an optical sensor adapted to make a plurality of measurements of the same optical property of the woven fabric with successive measurements falling along at least one line oriented substantially parallel to the direction of movement of the fabric;
   determining the difference between each of the measurements and the standard and establishing a factor corresponding to the difference;
   adding each established factor to a running total of such factors;
   comparing the running total to a preselected threshold value as each factor is added to the running total; and
   producing a signal if the running total exceeds the preselected threshold value.

10. The method of claim 9 further comprising the step of subtracting the factor corresponding to a measurement from the running total when a preselected number of subsequent factors have been added to the running total.

11. The method of claim 9 wherein the step of establishing a standard comprises the steps of:
    moving the fabric of acceptable quality past the optical sensor;
    making a plurality of measurements of the optical property of the sample with successive measurements falling along at least one line oriented substantially parallel to the direction of movement of the sample;
    calculating the average value of the plurality of measurements;
    calculating the standard deviation of the plurality of measurements; and
    wherein the calculated average value represents the standard.

12. The method of claim 11 wherein each of the differences is expressed in units of the calculated standard deviation and wherein the factors are proportional to the difference so expressed.

13. The method of claim 9 wherein the optical property is the intensity of light transmitted by the fabric.

14. The method of claim 9 wherein the optical property is the intensity of light reflected by the fabric.

15. An apparatus for detecting flaws in a sheet of web material, said apparatus comprising:
    means for establishing a standard indicative of the intensity of light transmitted by a sample of the web having acceptable quality;
    means for advancing the sheet of web material along a path;
    means for making a plurality of measurements of the intensity of light transmitted by the web material as the material moves along said path, said plurality of measurements falling along at least one line oriented substantially parallel to the direction of advancement of the sheet;
    means for comparing each of said measurements to said standard and establishing a factor characteristic of the deviation of the measurement from the standard;
    means for adding each of said factors to a running total of such factors;
    means for comparing the running total to a preselected threshold value as each of said factors is added to the total; and
    means for producing a signal when the running total exceeds the preselected threshold value.

16. The apparatus of claim 15 further comprising means for subtracting the factor characteristic of a deviation from the running total when a preselected number of subsequent factors have been added to the running total.

17. The apparatus of claim 16 wherein said means for making a plurality of measurements comprises an array of optical sensors arranged in closely spaced relationship into two rows with said rows being oriented substantially transversely relative to the direction of advancement of said sheet and with each sensor being closely adjacent the surface of said sheet, each of said sensors in said second row being offset relative to adjacent sensors in said first row, and means for illuminating the opposite surface of said sheet adjacent said sensor array.

18. The apparatus of claim 17 wherein each of said sensors is a photoresistor producing a voltage signal proportional to the intensity of light impinging thereon and wherein said means for illuminating said material is an elongated fluorescent bulb arranged in substantially spaced parallel relationship relative to said sensor array.

19. The apparatus of claim 18 wherein said means for establishing, comparing, adding and subtracting comprises a microprocessor electrically connected to said sensor array and adapted to measure the voltage signal produced by each sensor in said array as said sheet advances past said array.

* * * * *